(12) United States Patent
Derbyshire

(10) Patent No.: US 6,321,107 B1
(45) Date of Patent: Nov. 20, 2001

(54) DETERMINING LINEAR PHASE SHIFT IN CONJUGATE DOMAIN FOR MR IMAGING

(75) Inventor: J. Andrew Derbyshire, Baltimore, MD (US)

(73) Assignee: General Electric Company, Waukesha, WI (US)

(*) Notice: Subject to any disclaimer, the term of this patent is extended or adjusted under 35 U.S.C. 154(b) by 0 days.

(21) Appl. No.: 09/313,537

(22) Filed: May 14, 1999

(51) Int. Cl.$^7$ .................................................. A61B 5/055
(52) U.S. Cl. ......................... 600/410; 600/413; 324/307; 324/309
(58) Field of Search .................................. 600/410, 413; 324/307, 309, 312

(56) References Cited

U.S. PATENT DOCUMENTS

| | | | |
|---|---|---|---|
| Re. 35,656 | * 11/1997 | Feinberg et al. | 324/309 |
| Re. 36,679 | * 5/2000 | Zakhor et al. | 324/307 |
| 5,672,969 | * 9/1997 | Zhou et al. | 324/309 |
| 6,064,205 | * 5/2000 | Zhou et al. | 324/309 |
| 6,067,465 | * 5/2000 | Foo et al. | 600/410 |

* cited by examiner

Primary Examiner—Ruth S. Smith
(74) Attorney, Agent, or Firm—Jenkens & Gilchrist

(57) ABSTRACT

A method is provided for estimating or determining the linear phase shift of an MR signal pertaining to an object of interest. In accordance with the method, an MR sequence is applied to the object, to acquire a set of MR data samples in a specified domain, such as the time domain, the acquired data samples having an associated linear phase shift. A set of conjugate data samples is generated from the acquired data samples, in a domain conjugate to the specified domain such as the frequency domain. The linear phase shift is then determined from the conjugate data samples, by means of computations which are executed exclusively in the conjugate domain. The efficiency of such computations is comparable to the efficiency of the Ahn algorithm. The resultant linear phase shift is employed to reduce artifacts in constructing an MR image of the object, in connection with an MR technique such as navigator echo, or multi-echo imaging.

15 Claims, 3 Drawing Sheets

DETERMINING LINEAR PHASE SHIFT IN CONJUGATE DOMAIN FOR MR IMAGING

BACKGROUND OF THE INVENTION

The invention disclosed and claimed herein generally pertains to a method of magnetic resonance (MR) imaging, wherein acquired MR data has an associated linear phase shift which must be determined to reduce image artifacts, improve image quality or as a measure of some physical quantity. More particularly, the invention pertains to a method of the above type which significantly improves or enhances efficiency in determining linear phase shift. Even more particularly, the invention pertains to a method of the above type wherein MR data is acquired in one domain, such as the time domain, and the associated linear phase shift is determined in a domain conjugate thereto, such as the frequency domain.

As is well known by those of skill in the art, acquired MR image data may comprise complex valued signals, such as data acquired by sampling an MR signal in quadrature. Each data sample then comprises a complex value having an associated magnitude and phase. Complex valued signals are often considered to have two equivalent representations, referred to as the time domain and frequency domain representations, respectively.

As is further well known, certain MR imaging techniques require determination of linear or first order phase shift, that is, the variation of phase between adjacent MR data samples in a set of MR data. For example, linear phase shift is used in connection with a technique known as navigator echo, to determine the position of selected body structure of a patient which is subject to periodic or cyclical respiratory motion. Such positional information is essential, in order to minimize artifacts in providing an image of the moving structure. Typically, body structure associated with respiration comprises a patient's diaphragm, as well as organs such as the lungs and liver which move with the diaphragm. Such information is particularly useful for coronary artery MR imaging and general abdominal body MR imaging.

One such navigator echo technique, described in an article by Foo et al entitled "Navigator and Linear Phase Shift Processing", Proceedings of ISMRM, page 323 (1998), is based on the Fourier Transform Shift Theorem. Such technique is also described in U.S. patent application Ser. No. 08/980,192, filed Nov. 26, 1997 by Foo et al, and issued as U.S. Pat. No. 6,067,465 on May 23, 2000, which is commonly assigned herewith to the General Electric Company. In accordance with the Fourier Transform Shift Theorem, if an object centered about the origin of a coordinate system is displaced in a specified direction, then the Fourier transform of a function defining the object will have a linear phase shift that is equivalent to the amount of spatial displacement. Thus, in the Foo et al technique, a navigator echo signal associated with a moving structure of interest is acquired in the time domain. The acquired navigator echo is then Fourier transformed into the frequency domain, to provide a corresponding frequency profile or spectrum. The spectrum is truncated or apodized, such as by means of a band limiting filter, to remove any extraneous signal components. The truncated frequency profile is then Fourier transformed back to the time domain. Thereupon, linear phase shift is determined in the time domain, preferably by means of the Ahn algorithm. The position of the structure of interest, at the acquisition time of the navigator echo, may then be readily computed. The Ahn algorithm is a very well known technique for determining linear phase shift of a complex valued signal, and is described, for example, in "A New Phase Correction Method in NMR imaging based on Auto Correlation and Histogram Analysis", Ahn, et. al., IEEET Trans. Med. Imaging, 1987: MI-6: 32–36.

While the Ahn algorithm is known to be very computationally efficient, it will be seen that the navigator echo technique described above requires a Fourier transformation operation, from the frequency domain back to the time domain, before the Ahn algorithm can be applied. It would significantly enhance computational efficiency even further, if linear phase shift could be determined directly from frequency domain data so that the transformation back to the time domain would be unnecessary. In addition, certain multi-echo image sequences, such as echo planar imaging (EPI) and fast spin echo (FSE), also require determination of linear phase shift of the frequency domain spectrum (obtained from the time domain echo signal by Fourier transformation), for use in phase correction. In certain applications associated with these sequences, linear phase shift must be computed in near-real time, in order to provide phase correction of the multi-echo signals as image acquisition and reconstruction is being carried out. For these applications also, it would be very useful to be able to determine linear phase shift from data directly available in one domain, and to thus avoid the need to perform a Fourier transform back to the other domain. Significant reduction in processing time could thereby be achieved.

SUMMARY OF THE INVENTION

The invention provides a method for estimating or determining the linear phase shift of an MR signal with a level of computational efficiency which is comparable to the Ahn algorithm. It is particularly suitable to implementation in real-time signal processing applications. The method can be applied to the Discrete Fourier Transform ( DFT) of the samples that are employed in Ahn calculations. It is therefore assumed that the method will be of particular use when the sampled data exists in a domain which is conjugate to the domain for which the linear phase shift of the data is to be determined, and where an additional DFT would otherwise be required to evaluate the Ahn formula. It is considered to be entirely complementary to the existing Ahn procedure, while eliminating need for the additional DFT.

The method of the invention includes the step of applying an MR sequence to an object of interest, to acquire a set of complex valued MR data samples having an associated linear phase shift in a specified domain. The method further comprises generating a set of conjugate data samples, in a domain which is conjugate to the specified domain, from the acquired data samples. The linear phase shift is determined from the conjugate data samples, by means of computations which are executed or carried out exclusively in the conjugate domain, the linear phase shift then being employed to reduce artifacts in constructing an MR image of the object. In one useful embodiment, the set of acquired data samples is acquired in the time domain, and the generating step comprises applying a Fourier transform to the acquired data samples, to provide conjugate data samples which are in the frequency domain. However, the invention is not limited thereto.

In a preferred embodiment of the invention, the determining step comprises the steps of convolving adjacent conjugate data samples to provide a specified function, and then computing the value of the function at a specified spectral frequency to determine linear phase shift. Preferably, the spectral frequency is selected to be zero.

Embodiments of the invention may be usefully employed to reduce artifacts in connection with navigator echo techniques, and also in multi-echo imaging sequences.

DETAILED DESCRIPTION OF THE PREFERRED EMBODIMENT

Figure 1:
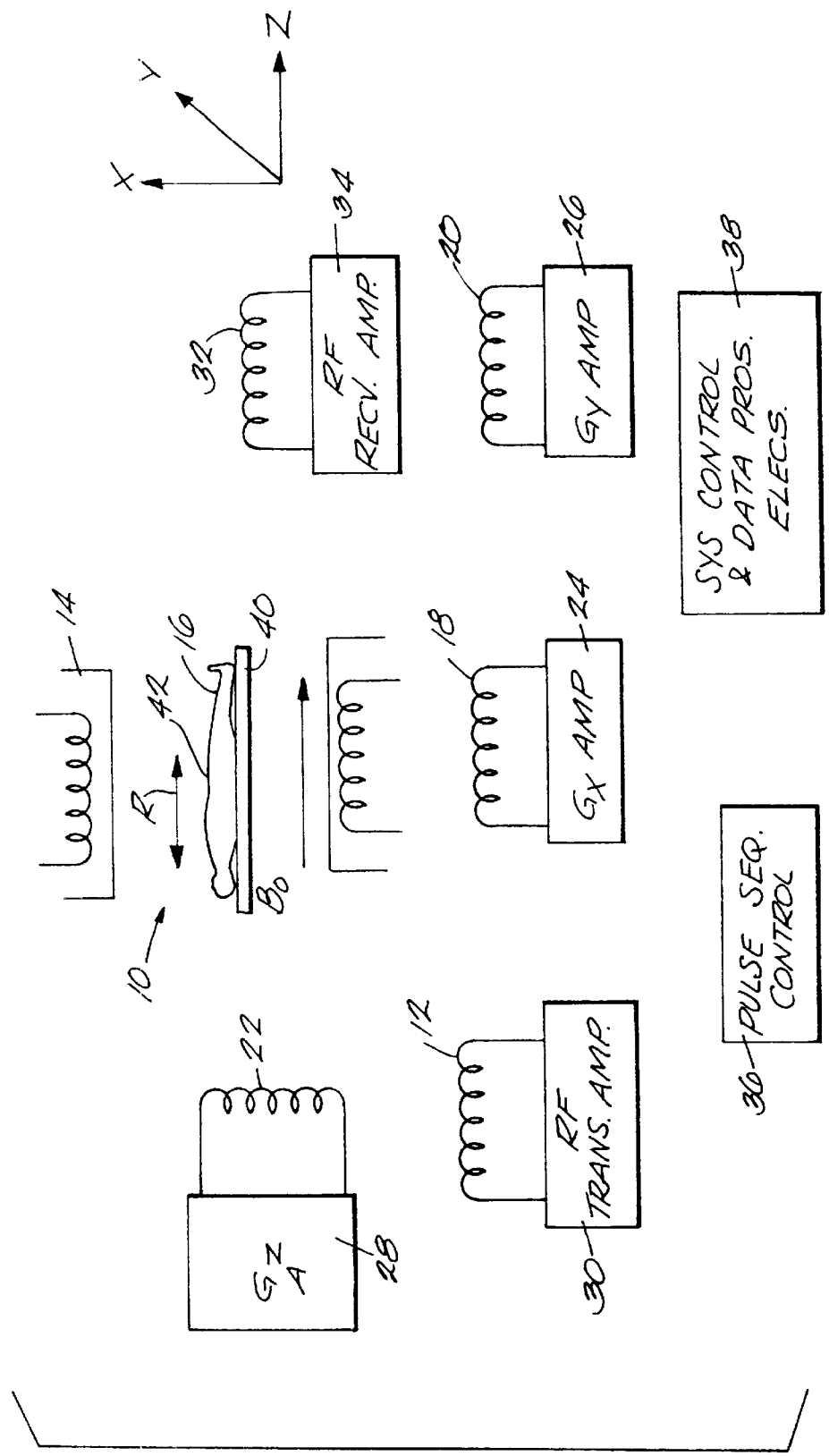
FIG. 1 is a schematic diagram showing basic components of an MR system for use in practicing an embodiment of the invention.

Referring to FIG. 1, there are shown the basic components of an MR system or scanner 10 which may be operated to acquire MR data in accordance with the invention described herein. System 10 includes an RF transmit coil 12, as well as a cylindrical magnet 14 for generating a main or static magnetic field $B_0$ in the bore thereof. RF coil 12 is operated to transmit RF excitation signals into a patient or other subject of imaging 16 residing in the magnet bore, in order to produce MR signals. System 10 further includes gradient coils 18, 20 and 22 for generating $G_x$, $G_y$, and $G_z$ magnetic field gradients relative to orthogonal X-, Y- and Z-reference axes, respectively. FIG. 1 shows each of the gradient coils 18, 20 and 22 respectively driven by gradient amplifiers 24, 26 and 28, and RF coil 12 driven by transmit amplifier 30. FIG. 1 further shows an RF coil 32, which is operated in association with a receive amplifier 34 to acquire MR signals from subject 16. In some arrangements, coil 32 and coil 12 comprise the same RF coil, which is operated in alternate modes during the imaging sequence. System 10 is further provided with a pulse sequence control 36, which is operated to control the RF and gradient amplifiers, and to thereby generate pulse sequences to produce and acquire sets of MR signals. System 10 also includes system control and data processing electronics 38 for operating respective components of system 10 to acquire MR data, to process the data in accordance with the invention, and to construct images therefrom. The construction, functions, and interrelationships of components of MR system 10 are well known and described in the prior art, such as in U.S. Pat. No. 5,672,969, issued Sep. 30, 1997 to Zhou et al.

Referring further to FIG. 1, there is shown patient 16 supported on a table 40 or the like so that the chest and cardiac region 42 of the patient is positioned within the bore of main magnet 14. The patient's diaphragm, as well as anatomic structure attached thereto such as the liver and lungs, moves along an axis R, during the course of successive respiratory cycles. Thus, displacement of the diaphragm and related structure, with respect to a reference position, varies periodically as a function of time. For purposes of description, the axis R is usefully considered to lie along the Z-axis of scanner 10.

As stated above, the navigator echo technique is very useful in MR imaging, such as in 3D MR coronary artery imaging or general abdominal body MR imaging, to determine the position of a patient's diaphragm. If the diaphragm is within a specified positional window (i.e., a particular range of positions relative to a reference position) when an MR image sequence is applied thereto, MR data produced by the sequence will be accepted for use in image reconstruction. Otherwise, the data will not be accepted. As also stated above, linear phase shift of a navigator echo, which is generated by a navigator pulse included in the image sequence, is computed by means of the Ahn algorithm, in order to provide a measurement of diaphragm displacement.

The Ahn algorithm provides a simple algorithm to calculate an estimate of the first order phase of a complex valued signal f(t), given samples $f_T$, where T=0, ..., N−1. The algorithm provides an estimate of the first order phase in the form of the linear phase shift per sample (i.e. the phase shift, $\delta\phi$ between $f_T$ and $f_{T+1}$) as follows:

$$\delta\phi = \arg\left[\sum_T f_{T+1} f_T^*\right] \qquad \text{Eqn. (1)}$$

Equation (1) can be understood by recognizing that each (complex valued) sample may be written as $f_T = A_T \exp(i\phi_T)$. For each T, an estimate of the phase shift per sample $\delta\phi$ is provided by $\delta\phi = \phi_{T+1} - \phi_T$. The product $f_{T+1} f_T^*$ is set forth as follows:

$$f_{T+1} f_T^* = A_T A_{T+1} \exp[i(\phi_{T+1} - \phi_T)] = A_T A_{T+1} e^{i\delta\phi_T} \qquad \text{Eqn. (2)}$$

In Eqn. (2), (*) denotes complex conjugation, and the product is a complex number with phase $\delta\phi_T$ and magnitude that is approximately the square of the local signal amplitude. (In fact, it is the square of the geometric mean of the two signal samples.) The Ahn method provides an estimate of $\delta\phi$ from the phase of the complex sum of these product terms.

The implicit magnitude squared weighting enhances the robustness of the Ahn method, since samples with low relative amplitude and, assuming uniformly distributed noise, low SNR are effectively suppressed. The method also avoids problems with phase wrapping, when the signal phase extends over a range in excess of $2\pi$. The method is also extremely efficient computationally: given complex samples as pairs of real and imaginary values, the algorithm requires only 4N (real) multiplications, 4N (real) additions and a single arctan computation.

Figure 2:
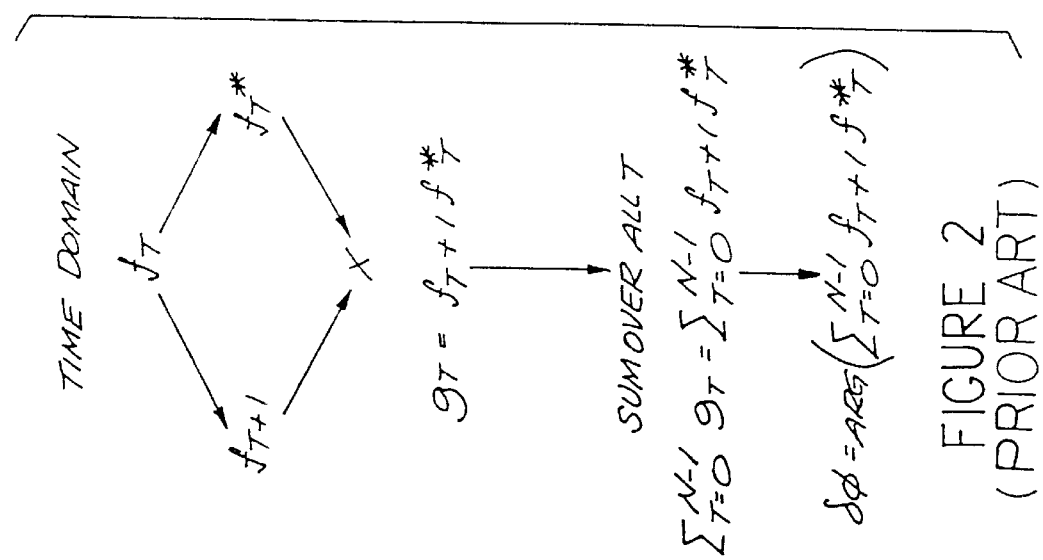
FIG. 2 is a flowchart showing the Ahn procedure in the time domain.

In the previously described navigator echo technique, the Ahn algorithm operates on data in the time domain to determine linear phase shift $\delta\phi$, in accordance with Equations (1) and (2). This operation is illustrated by the flowchart of FIG. 2. As shown therein, $g_T$, which is the product of $f_{T+1} f_T^*$, is summed over all sample times T. $\delta\phi$ is then derived as the argument of such summation.

Notwithstanding advantages of the Ahn algorithm, it has been recognized, in accordance with the invention, that it would be very desirable to provide an alternative method for detecting linear phase shift. More specifically, it could be highly beneficial to determine linear phase shift in a domain conjugate to the domain in which MR data is acquired, and at the same time to provide a level of computational efficiency which is comparable to the Ahn algorithm. As stated above, such method would reduce MR signal processing effort by eliminating need for certain Fourier transform operations.

In order to develop such method, further reference is made to Equation (1), wherein the term inside the summation (i.e., $f_{T+1} f_T^*$) may be interpreted as a pointwise multiplication of a time-shifted signal $f_T' = f_{T+1}$, and the complex conjugate of the original signal. These products are then summed over all the samples (i.e. the full extent of the sampled signal). Such pointwise multiplication, of a shifted copy of the time domain signal $f_{T+1}$ with the complex conjugate of the original time domain signal $f^*_T$ gives $g_T = f_{T+1} f^*_T$, as shown in FIG. 2.

The time-shifted signal in the time domain corresponds to a linear phase shifted spectrum in the frequency domain, while the complex conjugate signal corresponds to the complex conjugate of the frequency reversed spectrum. Accordingly, the pointwise multiplication in the time domain corresponds to a convolution in the frequency domain as follows:

$$g_T = f_{T+1} f^*_T \rightarrow (F_k e^{i2\pi k/N}) \otimes (F^*_{-k}) \qquad \text{Eqn. (3)}$$

$$(F_k e^{i2\pi k/N}) \otimes (F^*_{-k}) = \frac{1}{\sqrt{N}} \sum_{k'=0}^{N-1} F_{k'} e^{i2\pi k'/N} F^*_{-(k-k')} = G_k \qquad \text{Eqn. (4)}$$

In Eqn. (3), the arrow represents the Fourier transform operation, from the time domain into the frequency domain. In Eqns. (3) and (4), k represents the $k^{th}$ sample or spectral frequency, $k=0, \ldots, N-1$, $F_k$ is the magnitude thereof, and $2\pi k/N$ is the phase thereof.

In accordance with the invention, it has been recognized that summation over all samples in the time domain, that is, summation of all values as referred to above, corresponds to evaluation of the spectrum, in the frequency domain, at the specific frequency k=0. This provides the following relation:

$$\sum_{T=0}^{N-1} g_T = \sqrt{N} G_0 \qquad \text{Eqn. (5)}$$

Eqns. (4) and (5) provide the following relation:

$$\sqrt{N} G_0 = \sum_{k'=0}^{N-1} (F_{k'} F^*_{k'}) e^{i2\pi k'/N} = \sum_{k=0}^{N-1} |F_k|^2 e^{i2\pi k/N} \qquad \text{Eqn. (6)}$$

From the flowchart of FIG. 2 it is seen that $\delta\phi$ can be determined from $$\sum_{T=0}^{N-1} f_{T+1} f^*_T,$$

which is equal to $$\sum_{T=0}^{N-1} g_T.$$

From Eqn. (5), it is seen that $$\sum_{T=0}^{N-1} g_T,$$

in the time domain, is equivalent to $\sqrt{N} G_0$, in the frequency domain. Given such equivalency, together with Eqn. (6), linear phase shift $\delta\phi$, the phase shift per sample, can be determined in the frequency domain from the following relationship:

$$\delta\phi = \arg\left[\sum_{k=0}^{N-1} |F_k|^2 e^{i2\pi k/N}\right] \qquad \text{Eqn. (7)}$$

Figure 3:
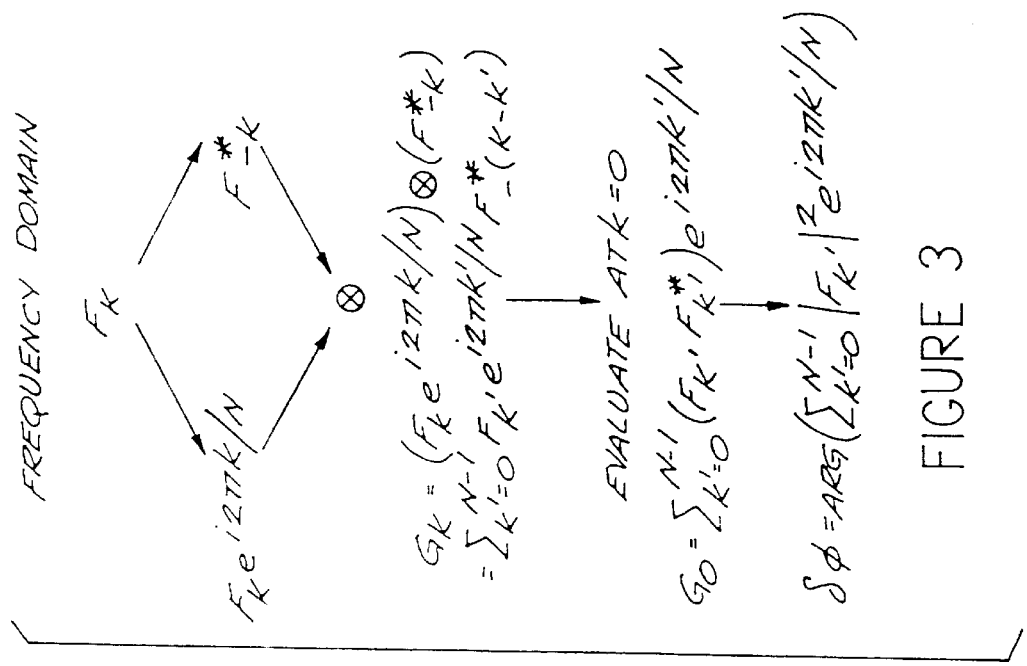
FIG. 3 is a flowchart showing a procedure, comprising an embodiment of the invention, in the frequency domain.

From Eqn. (7), linear phase shift can be determined exclusively from MR data samples in the frequency domain. Referring to FIG. 3, there is shown a flowchart which sets forth respective steps in deriving Eqn. (7). It will be seen that calculation of $\delta\phi$ therefrom involves the calculation of the squared magnitude at each sample point k, multiplication by a complex phasing factor and summation of the resulting complex values.

Since the phasing coefficients ($e^{i2\pi k/N}$) for Eqn. (7) can be precalculated (for any given N), linear phase shift $\delta\phi$ can be computed with a high level of efficiency. The coefficients can be stored as a table of cosine and sin values for each value of k, and the squared magnitude at each sample point is calculated as the sum of the squares of the real and imaginary components of $F_k$. This value is then multiplied by the appropriate cosine and sin coefficients and accumulated. Thus, the conjugate algorithm, as set forth in Eqn. (7), has similar efficiency to the original Ahn formulation, requiring only 4N (real) multiplications, 3N (real) additions and a single arctan computation. However, it is unnecessary to Fourier transform respective data samples back to the time domain, as is required for a number of important applications of the Ahn algorithm.

Figure 4:
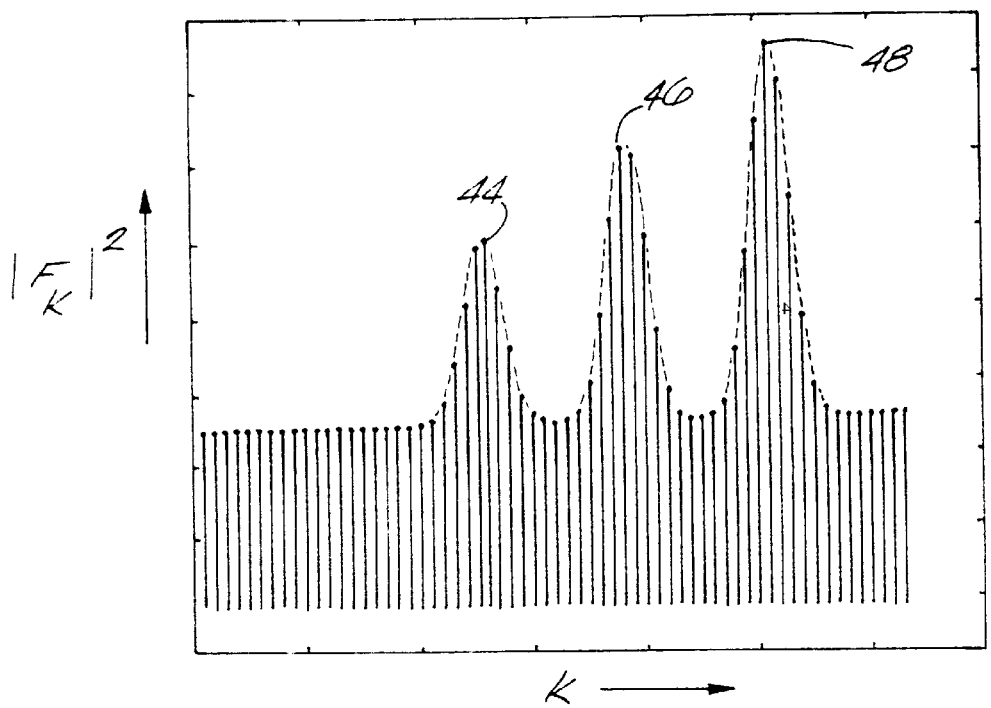
FIG. 4 is a graph showing a magnitude-squared signal in the frequency domain which is associated with the embodiment of FIG. 3.
Figure 5:
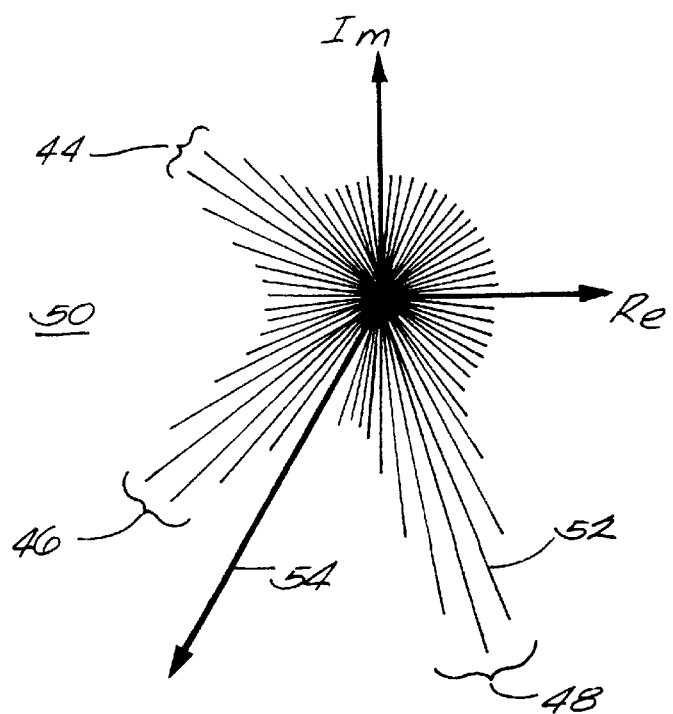
FIG. 5 is a diagram representing the data depicted in FIG. 4 in the complex plane.

In Equation (7), $(F_k)_{k=0}^{N-1}$ is the spectrum of the signal $(f_T)$, and the term $|F_k|^2$ is simply the magnitude squared at a given point k. Referring to FIG. 4, there is shown a graph comprising a plot of $|F_k|^2$ versus k, having peaks 44, 46, and 48. Each value $|F_k|^2$ is given a phase angle $2\pi k/N$ by multiplication with the complex exponential term. Such data can alternatively be represented as a fan of vectors in the complex plane, at equally spaced angles as k varies. The process can be interpreted as wrapping a magnitude squared profile around the unit circle in the complex plane. This is depicted in FIG. 5, which shows vectors 52 in the complex plane 50. Finally, the complex sum of superposition of the vectors is determined, and the argument of the resultant is evaluated.

The peaks labeled 44,46 and 48 in the graph of FIG. 4 respectively correspond to the similarly labeled bulges in FIG. 5. The bold vector 54 indicates the direction of the resultant of the superposition of the vectors, and is determined to provide $\delta\phi$.

In a modification of the invention, MR data could be provided in the frequency domain, and linear phase shift could be determined, in accordance with Equation (7), in the time domain.

Obviously, other modifications and variations of the present invention are possible in light of the above teachings. It is therefore to be understood that within the scope of the disclosed concept, the invention may be practiced otherwise than as specifically described.

What is claimed:

1. A method for constructing an MR image of a object comprising the steps of:

applying an MR sequence to said object to acquire a set of complex valued MR data samples in a specified domain, said acquired data samples having an associated linear phase shift;

generating a set of conjugate data samples in a domain which is conjugate to said specified domain from said acquired data samples;

determining said linear phase shift of said acquired data samples by convolving adjacent conjugate data samples to provide a specified function, and computing the value of said function at a specified spectral frequency to determine said linear phase shift; and employing said linear phase shift to reduce artifacts in constructing an MR image of said object.

2. The method of claim 1 wherein:

said set of acquired data samples is acquired in the time domain; and said generation step comprises applying a Fourier transform to said acquired data samples to provide said conjugate data samples, said conjugate data samples being in the frequency domain.

3. The method of claim 2 wherein:

said object is disposed to move through periodic motion cycles, and said linear phase shift is employed to determine the position of said object at a specified time during one of said motion cycles.

4. The method of claim 3 wherein:

a band limiting filter operation is applied to said conjugate data samples before determining linear phase shift therefrom.

5. The method of claim 4 wherein said object comprises structure disposed to move with a patient's diaphragm during successive respiratory cycles, and wherein:

said linear phase shift is used in connection with a navigator echo technique to construct said image from MR data acquired only when said object is located within a specified positional window.

6. The method of claim 2 wherein:

said spectral frequency is zero.

7. A method for constructing an MR image of an object comprising the steps of:

applying a multi-echo MR image sequence to said object to acquire a set of complex valued MR data samples in the time domain, said acquired data samples having an associated time shift, said time shift corresponding to a linear phase shift in the domain conjugate to that of the acquired data;

generating a set of conjugate data samples in said conjugate domain from said acquired data samples:

determining said linear phase shift by convolving adjacent conjugate data samples to provide a specified function, and computing the value of said function at a specified spectral frequency to determine said linear phase shift; and employing said linear phase shift to reduce artifacts in constructing an MR image of said object.

8. The method of claim 5 wherein:

said spectral frequency is zero.

9. Apparatus for constructing an MR image of an object comprising:

a set of MR components operable to acquire a set of complex valued MR data samples in a specified domain, said acquired data samples being associated with said object and having an associated linear phase shift;

a processor operable to generate a set of conjugate data samples in a domain which is conjugate to said specified domain from said acquired data samples, and to determine said linear phase shift of said acquired data samples by convolving adjacent conjugate data samples to provide a specified function, and to compute the value of said function at a specified spectral frequency; and said processor is further operable to construct an MR image of said object, and to employ said linear phase shift to reduce artifacts in said image construction.

10. The apparatus of claim 9 wherein:

said set of MR components is operated to acquire said complex valued MR data samples in the time domain; and said processor comprises means for applying a Fourier transform to said acquired data samples to provide said conjugate data samples, said conjugate data samples being in the frequency domain.

11. The apparatus of claim 10 wherein:

said object is disposed to move through periodic motion cycles, and said processor is operable to employ said linear phase shift to determine the position of said object at a specified time during one of said motion cycles.

12. The apparatus of claim 11 wherein:

said apparatus includes a filter for limiting said conjugate data samples to a specified bandwidth, before said processor is operated to determine linear phase shift therefrom.

13. The apparatus of claim 12 wherein said object comprises structure disposed to move with a patient's diaphragm during successive respiratory cycles, and wherein:

said set of MR components is operated in accordance with a navigator echo technique to determine the position of said object a selected times during said movement; and said processor is disposed to construct said image of said object only from MR data acquired when said object is located within a specified positional window.

14. The apparatus of claim 10 wherein:

said spectral frequency is zero.

15. The apparatus of claim 9 wherein:

said set of MR components is operated in accordance with a selected multi-echo MR image sequence.

* * * * *